United States Patent
Huber et al.

(10) Patent No.: US 10,073,110 B2
(45) Date of Patent: Sep. 11, 2018

(54) MOVABLE LOADING ELEMENT FOR LOADING AN AUTOMATED ANALYSIS SYSTEM

(71) Applicant: Roche Diagnostics Operations, Inc., Indianapolis, IN (US)

(72) Inventors: David Huber, Ebikon (CH); Marco Sangermano, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 57 days.

(21) Appl. No.: 15/240,013

(22) Filed: Aug. 18, 2016

(65) Prior Publication Data

US 2017/0059597 A1    Mar. 2, 2017

(30) Foreign Application Priority Data

Aug. 26, 2015    (EP) .................................... 15182497

(51) Int. Cl.
| | | |
|---|---|---|
| G01N 35/00 | (2006.01) | |
| G01N 35/04 | (2006.01) | |
| B01L 9/00 | (2006.01) | |
| G01N 35/02 | (2006.01) | |
| A47B 88/467 | (2017.01) | |

(52) U.S. Cl.
CPC ............ *G01N 35/0099* (2013.01); *B01L 9/00* (2013.01); *G01N 35/026* (2013.01); *G01N 35/04* (2013.01); *A47B 88/467* (2017.01); *B01L 2200/025* (2013.01); *G01N 2035/0425* (2013.01); *G01N 2035/0427* (2013.01); *G01N 2035/0465* (2013.01); *G01N 2035/0498* (2013.01)

(58) Field of Classification Search
None
See application file for complete search history.

(56) References Cited

U.S. PATENT DOCUMENTS

2015/0093834 A1    4/2015    Knecht et al.

FOREIGN PATENT DOCUMENTS

| EP | 2889626 A1 | 7/2015 |
|---|---|---|
| JP | 2003-083997 A | 3/2003 |
| WO | 2004/013640 A1 | 2/2004 |

OTHER PUBLICATIONS

Machine-generated English translation of JP 2003-83997 A, Specimen Pretreatment Apparatus, published Mar. 19, 2003.*

* cited by examiner

*Primary Examiner* — Kathryn Wright
(74) *Attorney, Agent, or Firm* — Roche Diagnostics Operations, Inc.

(57) ABSTRACT

A device for loading an automated analysis system is presented. The device comprises a chassis, a movable loading element movably coupled to the chassis and configured to move between a first and a second position, a holding structure, the holding structure being floatingly coupled to the movable loading element, the holding structure being configured to hold a receptacle for material to be loaded into the automated analysis system, a first alignment element attached to the chassis and a second alignment element attached to the holding structure. The first alignment element is configured to engage with the second alignment element to align the holding structure in a predetermined position relative to the chassis when the movable loading element is in the second position.

12 Claims, 8 Drawing Sheets

MOVABLE LOADING ELEMENT FOR LOADING AN AUTOMATED ANALYSIS SYSTEM

CROSS-REFERENCE TO RELATED APPLICATIONS

This application claims priority to EP 15182497.6, filed Aug. 26, 2015, which is hereby incorporated by reference.

BACKGROUND

The present disclosure generally relates to devices and methods for loading an automated analysis system and, in particular, to devices and methods for loading consumables into an automated analysis system.

In some automated analysis systems, material (e.g., consumables such as tips, vessels or other consumables) have to be loaded into the system to be used in an automated analysis process. For instance, some loading devices of automated analysis systems are equipped with a drawer for loading consumables into the automated analysis system. In these systems, an operator can store consumables in a rack and put the rack into the loading drawer. Subsequently, the operator closes the drawer and thereby moves the rack in the drawer into a working area of the automated analysis system. Then, the automated analysis system can manipulate the material loaded into the rack. For example, a robotic manipulator can grip the material loaded into the automated analysis system (e.g., grip pipette tips stored in the rack) for further processing.

Such robotic, or otherwise automated systems, can require a fairly precise placement of the material loaded into the system. In some cases, a manipulator of an automated analysis system can be taught to grip a particular piece of material in the loading drawer in a particular position. In some examples, the manipulator only tolerates fairly small deviations from a taught position (e.g., less than 100 µm). If this tolerated deviation is exceeded, the manipulator might cease to work properly and reliably. This can require re-teaching of the robotic manipulator and/or result in malfunctions of the automated analysis systems.

Therefore, there is a need for a manipulator of an automated analysis system (e.g., a robotic manipulator) that can encounter the material in precisely a taught position and can maintain a fairly high positioning precision after repeated actuations of the manipulator.

SUMMARY

According to the present disclosure, a device for loading an automated analysis system is presented. The device can comprise a chassis, a movable loading element movably coupled to the chassis and configured to move between a first and a second position and a holding structure. The holding structure can be floatingly coupled to the movable loading element. The holding structure can be configured to hold a receptacle for material to be loaded into the automated analysis system. The device can further comprise a first alignment element attached to the chassis and a second alignment element attached to the holding structure. The first alignment element can be configured to engage with the second alignment element to align the holding structure in a predetermined position relative to the chassis when the movable loading element is in the second position.

Accordingly, it is a feature of the embodiments of the present disclosure to provide for a movable loading element of an automated analysis system that can encounter the material in precisely a taught position and can maintain a fairly high positioning precision after repeated actuations of the movable loading element. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A device for loading an automated analysis system is presented. The device can comprise a chassis, a movable loading element movably coupled to the chassis and configured to move between a first and a second position and a holding structure. The holding structure can be floatingly coupled to the movable loading element. The holding structure can be configured to hold a receptacle for material to be loaded into the automated analysis system. The device can further comprise a first alignment element attached to the chassis and a second alignment element attached to the holding structure. The first alignment element can be configured to engage with the second alignment element to align the holding structure in a predetermined position relative to the chassis when the movable loading element is in the second position. This device for loading an automated analysis system can have one or more advantageous effects.

First, the alignment elements can secure that the holding structure and, hence, the material to be loaded attached to the holding structure can be positioned with a predetermined precision relative to the chassis. In this manner, a manipulator of an automated analysis system (e.g., a robotic manipulator) can encounter the material in precisely a taught position. This can be of particular importance in systems where a travelling path of the movable loading element is comparatively long. Thus, a risk of system malfunctions due to imprecisely placed material can be reduced or even eliminated.

Second, the holding structure and, thus, the material to be loaded can be decoupled from the movable loading element movably coupled to the chassis (e.g., from a drawer). In this manner, changes of the position of the material in the second position (e.g., when a drawer is closed) due to actuations of the drawer or other movable loading element can be avoided or at least minimized. Without these particular elements, forces induced in the movable loading element can be translated to the material and displace the material. For instance, a manually actuated drawer can move or deform when it is closed or after it has been closed, e.g., when an operator pulls the drawer unaware of the fact that it is already in a loading position. These movements and deformations can cause displacements of the material stored in the drawer large enough to cause malfunctions of an automated analysis system. For example, a piece of material might shift an overly large distance from a teaching point of a manipulator. Then, the manipulator might be unable to manipulate (e.g., grip) the material.

Third, the device for loading an automated analysis system can maintain a fairly high positioning precision after repeated actuations of the movable loading element. This can reduce a frequency with which a manipulator of the automated analysis system has to be taught and, in turn, reduce down-time of the automated analysis system.

The term "chassis" is used in the present disclosure to identify a part of the device for loading an automated analysis system which does not move when the movable loading element is moved between the first and the second positions. The term "chassis" may not be used as being limited to a particular function or a particular configuration of a part of the device for loading an automated analysis system. For example, a chassis can include a frame carrying different elements of the device for loading an automated analysis or an element attached to a frame carrying different elements of the device for loading an automated analysis. In other examples, a chassis can include a housing of the device for loading an automated analysis system.

The expression "floatingly coupled" can include any type of coupling that can allow the holding structure to move in one, two or all three orthogonal spatial directions relative to the movable loading element (e.g., a drawer the holding structure can be floatingly attached to). The holding structure can be floatingly coupled by the alignment elements (i.e., without a dedicated coupling element). For example, the alignment elements can sit loosely (e.g., movable by 1 mm or more in one or more spatial directions) in respective recesses of the movable loading element. In other examples, the holding structure can be floatingly coupled by one or more dedicated coupling element which can sit loosely in respective recesses of the movable loading element. Furthermore, the expression "floatingly coupled" can include but is not limited to floating bearings. For example, the holding structure can also be floatingly coupled by coupling via a flexible coupling element or by frictional coupling.

It can be merely required that the holding structure can move for a predetermined distance in one, two or all three spatial directions relative to the movable loading element when the alignment elements mate. In one example, the predetermined distance can be more than about 500 µm (e.g., more than about 1 mm or more than about 5 mm).

The expression "floatingly coupled" may not necessarily imply that the holding structure can move relative to the movable loading element without resistance. Rather, the holding structure can be floatingly coupled by, e.g., resilient, magnetic or frictional coupling. However, the forces holding the holding structure in place can be small enough so that they can be overcome when the alignment elements engage in the second position.

The movable loading element can be a drawer.

The second position of the movable loading element can be a closed position of the movable loading element.

The second alignment element can include a peg. The peg can be a conical peg. The conical peg can align the holding structure (in cooperation with a respective first alignment element of the chassis) in a predetermined position relative to the chassis in all three spatial directions. For instance, the positional accuracy can be about 500 µm or less or about 100 µm or less.

The first alignment element can include a recess configured to receive the second alignment element. The recess can be a hole configured to receive a corresponding member of the second alignment element.

The holding structure can be aligned in all three spatial directions when the movable loading element is in the second position. The holding structure can have a play of less than about 500 µm in each spatial direction when the first alignment element is engaged with the second alignment element. In this manner, particular types of manipulators of automated analysis systems (e.g., robotic manipulators) can reliably manipulate material stored in the movable loading device.

The movable loading element can be mechanically decoupled from the holding structure when the movable loading element is in the second position. In this context, the expression "mechanically decoupled" can mean that the movable loading element is not rigidly coupled to the holding structure. In this manner, forces induced in the movable loading element (e.g., a drawer) may not be directly translated to the holding structure. Material attached to the holding structure may substantially remain in place.

The device can include one or more additional first alignment elements and one or more additional second alignment elements arranged at different locations of the chassis and the movable loading element, respectively. Each of first alignment elements can be configured to engage with a corresponding second alignment element to secure the holding structure relative to the chassis when the movable loading element is in the second position. At least one of the second alignment elements can be arranged at a forward portion of the holding structure and at least a second one of the second alignment elements can be arranged at a rearward portion of the holding structure in a direction of movement of the movable loading element. Distributing multiple alignment elements over the extent of the holding structure can further improve the alignment precision of the holding structure relative to the chassis. For instance, a reduction of the alignment precision due to deformations of the holding structure itself in response to stress and strain induced into the holding structure can be diminished or even be avoided.

The device can further comprise a retaining element configured to keep the first alignment element in engagement with second alignment element when the holding structure is in the predetermined position. A retaining element can secure that an alignment element of the holding structure remains in alignment with a respective alignment element of the chassis. However, in some examples, the alignment elements can be configured and arranged so that the alignment elements keep the holding structure in alignment with the chassis without a dedicated retaining element. The retaining element can be coupled between the holding structure and the movable loading element. The retaining element can include at least one resilient element configured to keep the first alignment element in engagement with second alignment element when the movable loading element is in the second position. The retaining element can be configured to push or pull the first alignment element in engagement with second alignment element when the movable loading element is in the second position.

The movable loading element can be configured to be manually actuated. The alignment precision can be particularly advantageous for manually actuated movable loading elements. In some prior art devices, manually operated movable loading elements material loaded into a movable loading element can be imprecisely positioned as a result of variable forces transmitted by the operator to the movable loading element. For instance, a particular operator might close the movable loading element with excessive force resulting in an imprecise positioning of the material or a fast degradation of positioning precision. The device of the present disclosure can decouple the movable loading element from the holding structure. Therefore, even if an operator acts on the movable loading element with excessive force, this might not influence the positioning precision of material loaded into the movable loading element.

However, even if the device for loading an automated analysis system might have particular advantages for manually operated device movable loading elements, automatic movable loading elements can also benefit from the teachings of the present disclosure. For instance, an automated movable loading element can be constructed in a simpler manner when the positioning precision of material loaded into the movable loading element can be secured as described herein.

Loading an automated analysis system can be configured to be at least partially passively actuated (e.g., actuated exclusively by an operator). The device for loading an automated analysis system can achieve a desired positioning precision even without elaborate automated mechanisms (e.g., a fully automated closing mechanism for a drawer).

The device for loading an automated analysis system can further comprise a locking device for locking the movable loading element to the chassis when the movable loading element is in the second position. A locking device can prevent that the movable loading element is removed from the second position when a manipulation process of material loaded in the movable loading element is ongoing. It can be noted, however, that a locking device may not be required to provide the alignment precision of the holding structure relative to the chassis. In some examples in which the alignment elements are only configured to align the holding structure in one or two orthogonal spatial directions, the locking device can additionally align the holding structure in the respective remaining spatial direction(s). The locking device can be an electrically actuated locking device. The locking device can include a fixed element coupled to the movable loading element and a movable element coupled to the chassis.

The device for loading an automated analysis system can further comprise a sensor element for detecting a position of the movable loading element relative to the chassis. The sensor element can include an optoelectronic sensor.

The device for loading an automated analysis system can further include an optical indicator configured to indicate that the movable loading element is in the second position.

The device for loading an automated analysis system can further include a self-closing mechanism for moving the movable loading element over at last part of its travelling path into the second position. A self-closing mechanism can secure that the last part of the travelling path of the movable loading element is traversed in a reproducible manner. In particular, excessive forces acting on the alignment elements or other parts of the device for loading an automated analysis system can be avoided (which might possibly lead to an impaired positioning precision, e.g. after a number of loading processes). In addition or alternatively, a self-closing mechanism can secure that the movable loading element reliably travels into the second position in cases in which manually operated movable loading elements are used. Moreover, a self-closing mechanism can also improve usability. However, a self-closing mechanism is an optional feature of the devices for loading an automated analysis system described herein and not essential for realizing the advantages described in the present disclosure. The self-closing mechanism can be a mechanical self-closing mechanism. The self-closing mechanism can include a first element attached to the chassis and a second element attached to the movable loading element.

The first element, the second element, or both can be configured to be spanned by a movement of the movable loading element during a first part of the travelling path of the movable loading element and the respective element can further be configured to relax and thereby move the movable loading element over the last part of its travelling path into the second position. In this manner, a simple and reliable operation of the self-closing mechanism can be secured without requiring, e.g., electrically actuated parts. The first element of the self-closing mechanism can be stationary and the second element of the self-closing mechanism can be movable. The first element or the second element of the self-closing mechanism can have a recess configured to grip a corresponding protrusion of the respective other element of the self-closing mechanism to move the movable loading element over the last part of its travelling path into the second position. The self-closing mechanism can be actuated by a resilient element.

The holding structure can be floatingly coupled such that the holding structure can move in two or more orthogonal directions relative to the movable loading element when the movable loading element is in the first position.

The first position of the movable loading element can be a loading position. When using the device for loading an automated analysis system of the present disclosure, a loading process of the material into the movable loading device can be (at least partially) separated from an alignment process of the material relative to, e.g., a robotic manipulator of an automated analysis system. In this manner, interference of the user with the loading device during the loading process can have little or no impact on the placement precision of the material.

The holding structure can have one or more attachment elements to attach one or more receptacles for material to be loaded into the automated analysis system at a predetermined position to the holding structure.

The material to be loaded into the automated analysis system can include one or more selected from the list comprising vessels, pipette tips, and needles.

The holding structure can be substantially plate-shaped.

The chassis and/or the movable loading element can include one or more stops to limit a movement of the movable loading element.

The device for loading an automated analysis system can include one or more coupling elements to floatingly couple the holding structure to the movable loading element. The one or more coupling elements can be the alignment elements sitting in respective recesses of the movable loading element.

A system for automated sample analysis can comprise one or more device for loading an automated analysis system and one or more automated manipulation devices to manipulate material included in the receptacle when the holding structure is secured relative to the chassis. The one or more automated manipulation devices can include at least one vessel gripper and/or at least one pipette nozzle or needle.

A device for loading disposables into an automated analysis system device is presented. The device can include a chassis, a drawer movably coupled to the chassis, and a holding structure. The holding structure can be floatingly coupled to the drawer. The holding structure can be configured to hold a receptacle for material to be loaded into the automated analysis system. The device can further include a first alignment element attached to the chassis and a second alignment element attached to the holding structure. The first alignment element can be configured to engage with the second alignment element to align the holding structure in a predetermined position relative to the chassis when the drawer is in a closed position. The device can further include a retaining element coupled between the holding structure and the drawer and configured to push the first alignment element in engagement with second alignment element when the drawer is in the closed position.

A method for loading an automated analysis system is presented. The method can comprise loading material to be loaded into the automated analysis system into a movable loading element by attaching receptacles for the material to a holding structure floatingly coupled to the movable loading element, closing the movable loading element, and aligning the holding structure in a predetermined position relative to a chassis of the automated analysis system by engaging a first alignment element attached to the chassis with a second alignment element attached to the movable loading element when the movable loading element is in a closed position. The holding structure can be substantially decoupled from the movable loading element when the movable loading element is in a closed position.

The method can further comprise gripping the material by an automated gripper of the automated analysis system when the movable loading element is in a closed position.

The method can further comprise automatically inserting a pipette or needle into the material when the movable loading element is in a closed position.

Different aspects of the devices and methods for loading an automated analysis system of the present disclosure will subsequently be discussed. First, the operation of example devices for loading an automated analysis system of the present disclosure will be discussed in connection with FIGS. 1 to 3. Subsequently, in connection with FIGS. 4 to 8, different example elements of a device for loading an automated analysis system of the present disclosure will be explained. First, in connection with FIGS. 4 to 6 aspects of a holding structure according to the present disclosure will be discussed. Then, in connection with FIG. 7, an example of movable loading element will be treated in more detail. Last, features of an example chassis will be detailed based on FIG. 8.

Figure 1:
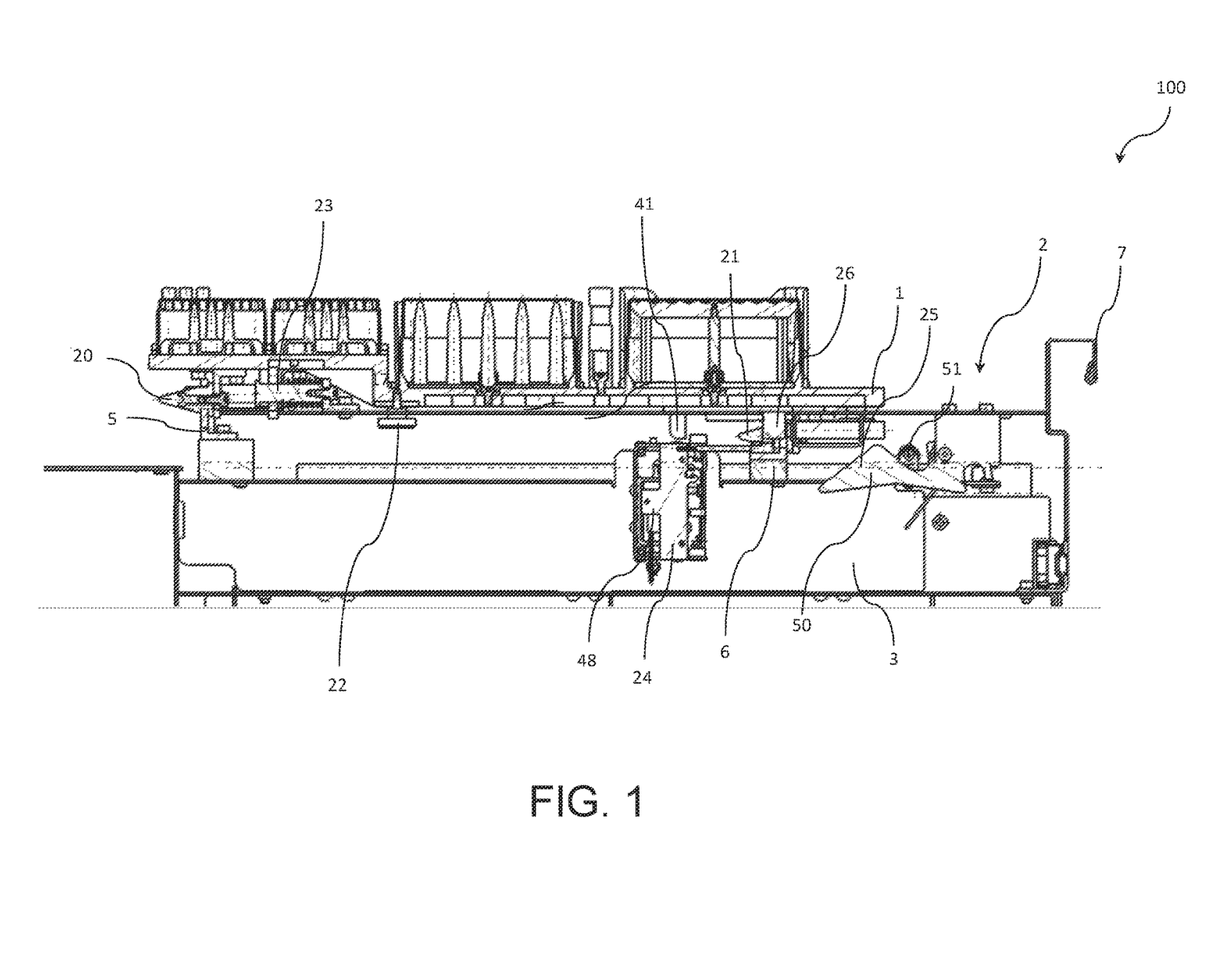
FIG. 1 illustrates an example device for loading an automated analysis system according to an embodiment of the present disclosure.

FIG. 1 illustrates an example device for loading an automated analysis system according to the present disclosure. The movable loading element of FIG. 1 can includes a chassis 3, a movable loading element 2 movably coupled to the chassis 3 and configured to move between a first and a second position, a holding structure 1, the holding structure 1 being floatingly coupled to the movable loading element 2, wherein the holding structure 1 is configured to hold a receptacle for material to be loaded into the automated analysis system, a first alignment element 5, 6 attached to the chassis and a second alignment element 20, 21 attached to the holding structure 1, the first alignment element 5, 6 being configured to engage with the second alignment element 20, 21 to align the holding structure 1 in a predetermined position relative to the chassis 3 when the movable loading element 2 is in the second position.

In the examples device of FIG. 1, the movable loading element 2 can be a drawer that can be configured to move linearly between the first and the second positions. However, the movable loading element can also be a movable loading element that can rotate between the first and second positions. For example, the movable loading element can be configured to rotate out of a closed position (the second position) into an open position (the first position), and vice versa. In still other examples, the movable loading element can be configured to describe a trajectory including linear and rotational movement to move from the first position into the second position. These movable loading elements other than a drawer can also be equipped with the floating holding structures and the alignment elements of the present disclosure.

The first position of the drawer 2 can be an open position and the second position of the drawer 2 can be a closed position. In general, the second position can be the position in which the material held by the holding structure can be manipulated in the device for loading an automated analysis system. This position does not have to be a closed position of a drawer 2 or any other movable loading element. In some examples, the movable loading element can simply move along a predetermined path to arrive in the second position in which the holding structure 1 is aligned relative to the chassis 3. For instance, an operator of the device for loading an automated analysis can load material onto receptacles attached to the holding structure and move the movable loading element into the second position by translation and/or rotation of the movable loading element. In the second position, a manipulator of the automated analysis system can manipulate the material. Spatially separating the loading position of the material and the position in which the material is manipulated by the automated analysis system can be advantageous as the areas of the automated analysis system where the material is manipulated might not be easily accessible.

The chassis 3 of the device for loading an automated analysis system may not move when the drawer 2 is actuated. In one example, a manipulator (e.g., a robotic manipulator—not shown in FIG. 1) can also be attached to the chassis 3. In still other examples, the chassis 3 of the device for loading an automated analysis system can be rigidly connected to a module of the automated analysis system carrying a manipulator (e.g., a robotic manipulator).

The holding structure 1 of FIG. 1 can include a plate onto which one or more receptacles for material to be loaded into the automated analysis system can be stored. In other words, the holding structure 1 can support the one or more receptacles for material to be loaded into the automated analysis system from below. In other examples, the holding structure can have a different configuration. For example, the holding structure can support receptacles for material to be loaded into an automated analysis system from a side or from above instead of from below. In addition or alternatively, the holding structure can include a frame instead of a plate into which the receptacles can be mounted. In still other examples, the holding structure can have the form of a box.

In the example of FIG. 1, the device for loading an automated analysis system can include multiple first alignment elements 5, 6 and multiple second alignment elements 20, 21. The second alignment elements 20, 21 attached to the holding structure 1 can include conical pegs. The first alignment elements 5, 6 attached to the chassis can include circular recesses. The first and second alignment elements can be shaped and arranged in multiple other ways. This will be discussed below in connection with FIGS. 4 to 8.

Figure 3:
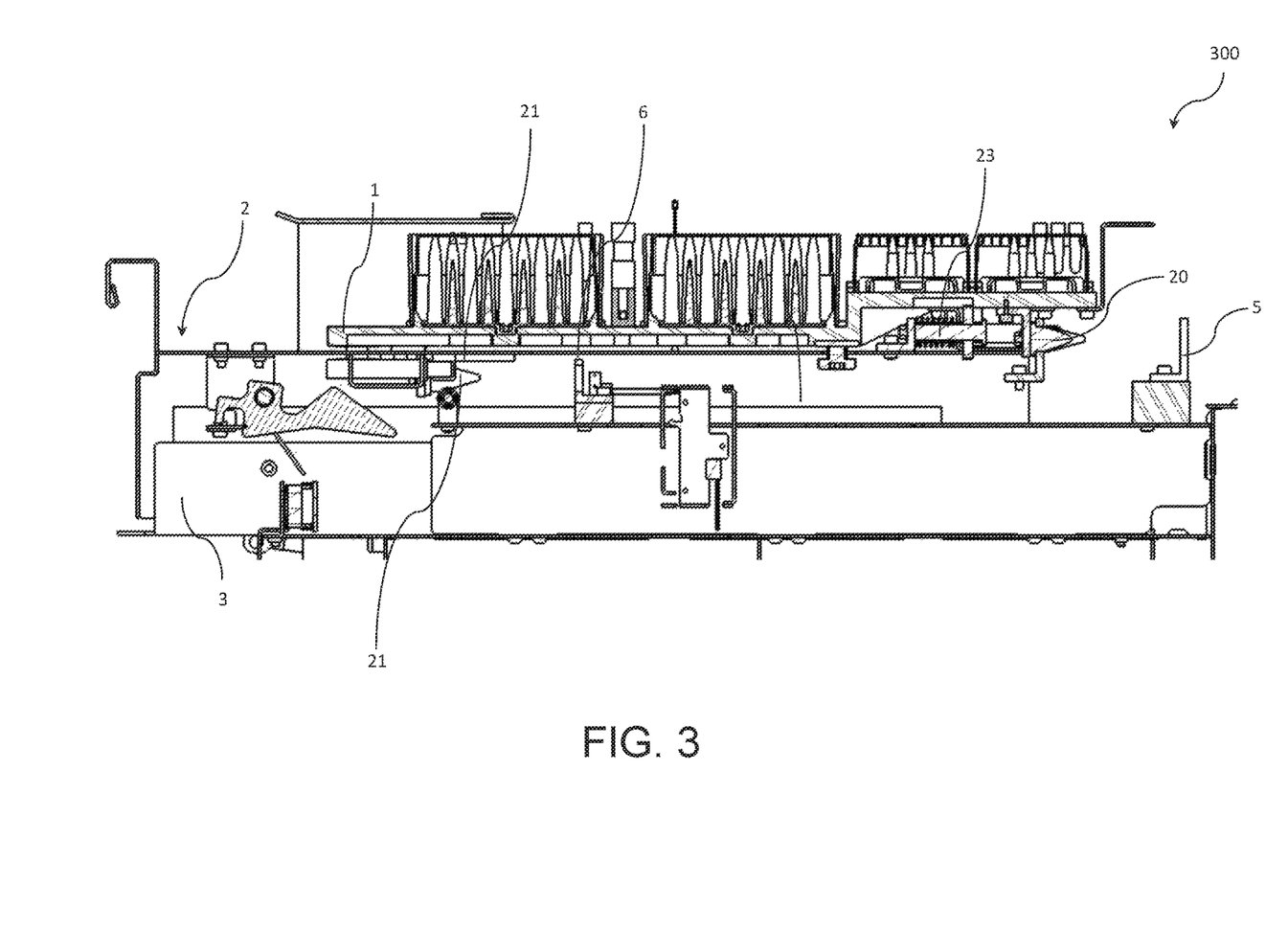
FIG. 3 illustrates the device for loading an automated analysis system of FIG. 1 in a non-closed state according to an embodiment of the present disclosure.

After having presented the main elements of the device for loading an automated analysis system of the present disclosure, the operation of the device will subsequently be discussed in more detail in connection with FIG. 3. FIG. 3 shows the device for loading an automated analysis system of FIG. 1 in a non-closed state.

As can be seen, the drawer 2 has been moved out of the first position (e.g., an open position) and approaches the second position (e.g., a closed position). This can happen as the result of manual actuation by an operator. In other examples, the drawer 2 can be coupled to an automatic closing actuator (e.g., an electric actuator or a pneumatic or hydraulic actuator).

In FIG. 3, the conical pegs 20, 21 and the corresponding recesses 5, 6 attached to the chassis 3 have not yet come into contact. This can happen when the drawer 2 is moved further to the right from its position shown in FIG. 3. Then, the conical pegs 20, 21 can engage with the recesses 5, 6 and the drawer 2 reaches the second position (e.g., a closed position). In this second position, the drawer 2 can be aligned with the chassis 3 as the conical pegs 20, 21 assume a predetermined position inside the recesses 5, 6. The previously floating holding structure 1 can no longer move relative to the chassis 3. The drawer 2 in the second (e.g., closed) position is depicted in FIG. 1.

In this state, a positioning precision of the holding structure can be determined solely by the play of conical pegs in the recesses (which might be fairly small). Accordingly, a precision with which material to be loaded into the automated analysis system is positioned relative to the chassis 3 can be determined by the play of the conical pegs in the recesses plus a precision of the placement of the material on the holding structure 1. In one example, the material to be loaded can have a play of less than about 500 µm in all spatial directions (or less than about 100 µm in all spatial directions) when the first alignment element is engaged with the second alignment element.

In order to secure the holding structure's 1 alignment in the second position, the device for loading an automated analysis system can be equipped with a resilient element 23 configured to keep the first alignment elements 5, 6 in engagement with second alignment elements 20, 21 when the movable loading element is in the second position. For instance, the resilient element 23 can be attached to the drawer 2 such that the resilient element can be compressed when the drawer 2 approaches the second position. The resilient element 23 can be arranged to come in contact with the holding structure 1 when the drawer 2 approaches the second position.

In one example, the resilient element 23 can be pushed against a corresponding element of the holding structure. As a result of this pushing action, the resilient element 23 can be compressed. In a compressed state, the resilient element 23 can induce a predetermined force in a direction opposite of a direction of movement of the drawer 2. This can push the first and second alignment elements 5, 6, 20, 21 into engagement. By this operation, the resilient element 23 can secure a proper engagement of the first and second alignment elements 5, 6, 20, 21 and thus a proper alignment between the chassis 3 and the holding structure 1.

In the example of FIG. 1, the resilient element 23 can include a spring. However, it is not necessary to use a spring or even a resilient element to effect the securing of the first and second alignment elements 5, 6, 20, 21 discussed above. In general, any retaining element configured to secure an engagement of the first and second alignment elements 5, 6, 20, 21 can be used. Further examples of retaining elements will be discussed in connection with FIG. 7 below.

Figure 2:
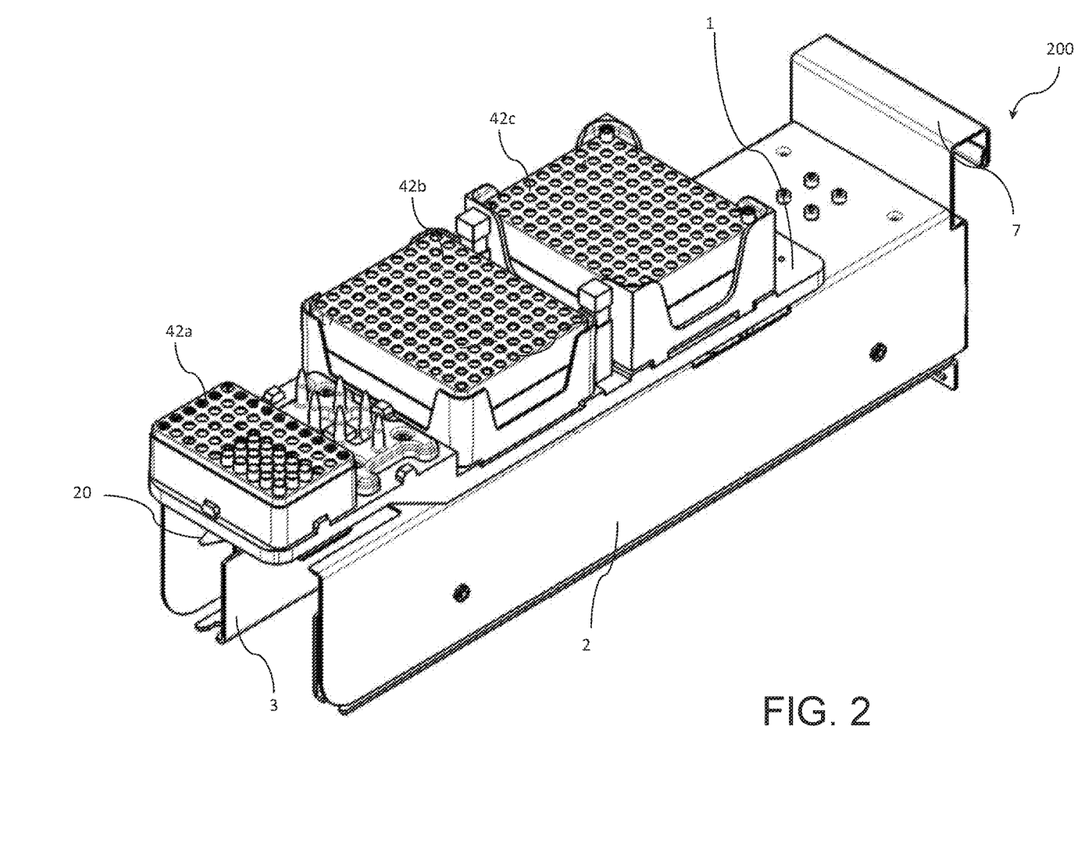
FIG. 2 illustrates a second view of the device for loading an automated analysis system of FIG. 1 according to an embodiment of the present disclosure.

As can be seen in FIGS. 1 to 3, the device for loading an automated analysis system according to the present disclosure can have several additional optional components. These components will be discussed subsequently.

First, the device for loading an automated analysis system of FIG. 1 can include a self-closing mechanism 25 for moving the movable loading element 2 over at last part of its travelling path into the second position. In one example, the self-closing mechanism 25 can draw may not require an action of an operator (or any active actuator) during this last part of its travelling path. In this manner, the drawer 2 can be securely closed even if an operator has not properly closed the drawer 2. In addition, the self-closing mechanism 25 can secure that a last part of the travelling path of the drawer 2 can be traversed in a controlled manner (e.g., to a well-controlled end position without applying excessive force to, e.g., stops arranged at the chassis 3).

The example self-closing mechanism 25 of FIG. 1 can include a rotatable element 50 attached to the chassis 3 and a stationary element 51 attached to the drawer 2. As can be seen in FIG. 2, the rotatable and stationary elements 50, 51 can be arranged to contact each other when the drawer 2 approaches the closed position. The rotatable element 50 can be configured to rotate in this situation and the rotatable element 50 can drag the stationary element 51 with it to move the drawer 2 (to which the stationary element 51 is fixed) by this rotation into the second position.

In one example, a resilient element (e.g., a spring) can be coupled between the chassis 3 and the stationary element 51. The resilient element can be arranged to be in a compressed state to effect a rotation of the rotatable element 50 which in turn can move the stationary element 51 and thus the drawer 2 to bring it in the second position.

The example rotatable element 50 of FIG. 1 can have an asymmetric groove into which the stationary element 51 of the drawer 2 can be dragged. Once the stationary element 51 has come into contact with an edge of the asymmetric groove, the rotation of the rotatable element 50 can result in the stationary element 51 being dragged along the edge until it comes to rest in a valley of the groove. This can conclude the self-closing actuation.

In one example, the resilient element can be arranged to be spanned by the movement of the drawer 2. For instance, as shown in FIG. 2, the self-closing mechanism 25 can be in a relaxed state when the drawer 2 is located a predetermined distance away from its closed position (or any others second position). When the drawer 2 is moved further in direction of its closed position, the stationary element 51 mounted on the drawer (or another suitable element) can come into contact with the rotatable element 50 and span the resilient element. In the example of FIG. 2, the rotatable element can receive a downward push by the stationary element 51. As a result of this downward push, the rotatable element 50 can rotate whereby the resilient element coupled between the rotatable element 50 and the chassis can be spanned. If the drawer 2 is moved further towards a closed position, the resilient element can release its potential energy and thereby force the rotatable element 50 to rotate and effect the above discussed self-closing action.

Even though FIG. 1 and FIG. 2 depict a particular self-closing mechanism, the devices for loading an automated analysis system according to the present disclosure can also include different self-closing mechanisms. In one example, the arrangement of the rotatable element 50 and the stationary element 51 can be reversed (i.e., the rotatable element can be attached to the drawer 2 and the stationary element can be attached to the chassis 3). In still other embodiments, the self-closing mechanism can include elements that can be shaped and arranged differently or be actuated in a different way than by a resilient element. For instance, the self-closing mechanism can include a first element which can be configured to push or pull the drawer into the second position. In still other examples, the self-closing mechanism can include one or more magnetic elements which can be configured to actuate the self-closing mechanism.

After having discussed the self-closing mechanism, an additional optional locking device 24 for locking the movable loading element to the chassis when the movable loading element is in the predetermined position will be discussed next.

The example locking device 24 of FIG. 1 can include an electrically actuated lock 48 attached to the chassis 3. The electrically actuated lock 48 can be configured to grip a fixed element 41 (e.g., a fin) attached to the drawer 2. In the example of FIG. 1, the lock 48 can be configured to move upward to engage with the fixed element 41. In this manner, the drawer 2 can be locked relative to the chassis 3 in the second position. This can prevent an operator from accidentally opening the drawer 2 while the material loaded in the drawer is still being manipulated, thereby disturbing the manipulation process. In some examples, the device for loading an automated analysis system can include an optical indicator (e.g., one or more light emitting diodes) that can be configured to indicate when the locking device 24 is in a locked position.

Even though in the example of FIG. 1 the locking device 24 has a particular configuration, the devices for loading an automated analysis system can also be configured and arranged in different ways. For example, the locking device can be mechanically actuated. Moreover, the locking device can be configured to engage with a fixed element arranged at a different side of the drawer than the lower side (e.g., an upper side or a lateral side). The devices for loading an automated analysis system can also include more than one locking device.

Additionally or alternatively, the devices for loading an automated analysis system can include one or more coupling elements to floatingly couple the holding structure to the movable loading device.

Figure 7:
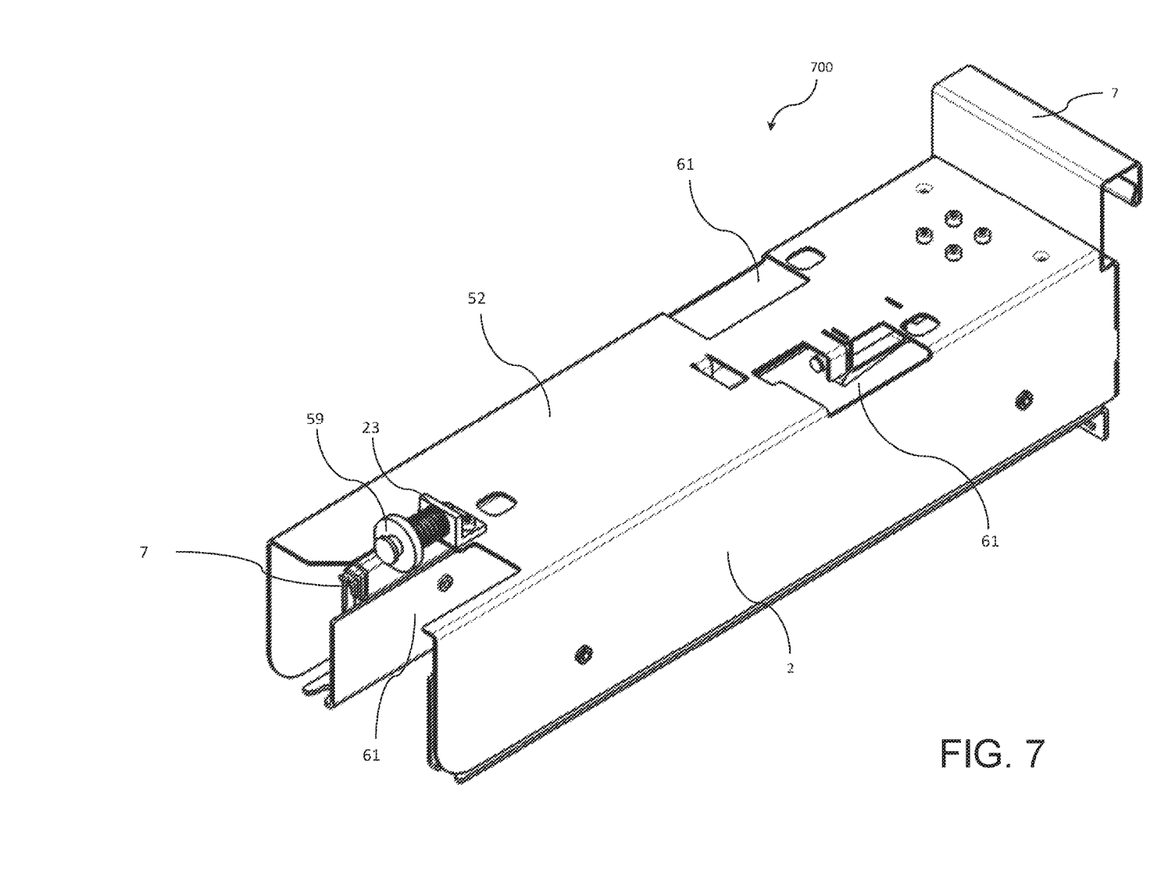
FIG. 7 illustrates an example movable loading element according to an embodiment of the present disclosure.

In the example of FIG. 1, the conical pegs 20, 21 (i.e., the alignment elements) can serve as coupling elements to floatingly couple the holding structure 1 to the drawer 2. Each conical peg 20, 21 can extend through a respective recess in the drawer 2 (the recesses are depicted in FIG. 7 below). Thus, the holding structure 1 can loosely sit on the drawer (e.g., the holding structure 1 can move at least 1 mm or at least 5 mm in one or more spatial directions) and thereby can floatingly couple the holding structure 1 to the drawer 2.

In examples with other alignment elements than the conical pegs shown in FIG. 1, these other alignment elements can also serve as coupling elements in the manner described above. In still other examples, the device for loading an automated analysis system can include one or more dedicated coupling elements for floatingly coupling the holding structure and the movable loading element. In one example, the one or more dedicated coupling elements attached to the holdings structure can extend through recesses of the movable loading element. Additionally or alternatively, one or more dedicated coupling elements attached to the movable loading element can extend through recesses of the holding structure. In still other examples, the coupling element can include one or more resilient elements that can floatingly couple the holding structure and the movable loading device. In still other examples, the coupling element can include one or more magnets that floatingly couple the holding structure and the movable loading device.

Moreover, the device for loading an automated analysis system of the present disclosure may not necessarily require a dedicated coupling element to floatingly couple the holding structure 1 and the movable loading device. For example, both elements can be frictionally coupled to provide a floating coupling between them. In this example, the frictional coupling can allow that the holding structure can be dragged with the movable loading element when the movable loading element is actuated. On the other hand, the frictional coupling can be overcome by the alignment elements (possibly in co-operation with a restraining element) to align the holding structure.

In the preceding sections different components have been discussed which lock the movable loading element (e.g., drawer 2) relative to the chassis 3, or limit a movement of the movable loading element (e.g., drawer 2) relative to the chassis 3. The operation of these components, however, can be substantially independent of the alignment operation of the holding structure 1 relative to the chassis 3 effected by the alignment elements. After all, the holding structure can be substantially decoupled from the drawer when the drawer is in the second (e.g., closed position). For example, in the example of FIG. 1 the holding structure can be coupled to the drawer by resilient element 23 when the drawer is in the second position. Thus, even when the drawer 2 and the chassis 3 are coupled (e.g., by actuation of the locking device 24 or the stop 22), the holding structure can still be aligned with a predetermined precision (as discussed above) by the alignment elements.

In the preceding sections the interplay between a movable loading element (e.g., drawer 2), a chassis 3 and a holding structure 1 of an example device for loading an automated analysis system has been detailed. The different components of the device for loading an automated analysis system of the present disclosure will be discussed in more detail in the following sections.

Figure 4:
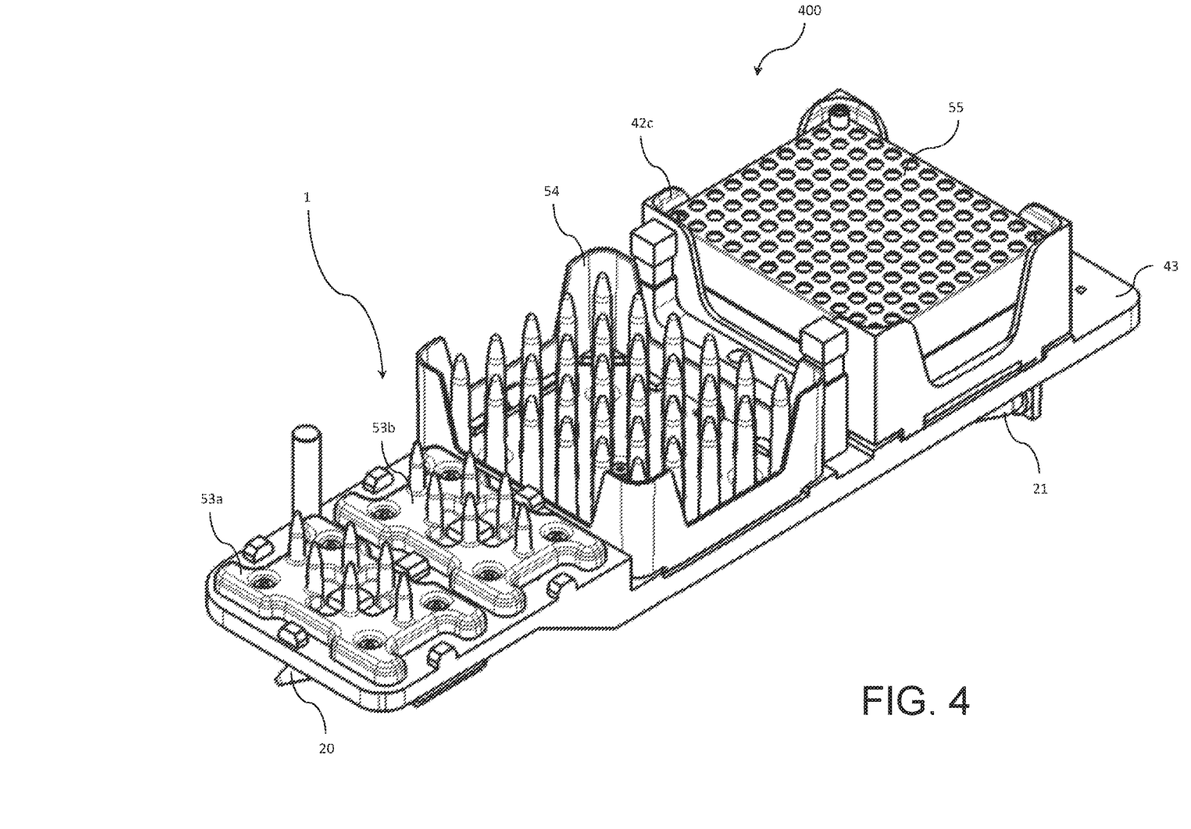
FIG. 4 illustrates an example holding structure according to an embodiment of the present disclosure.
Figure 5:
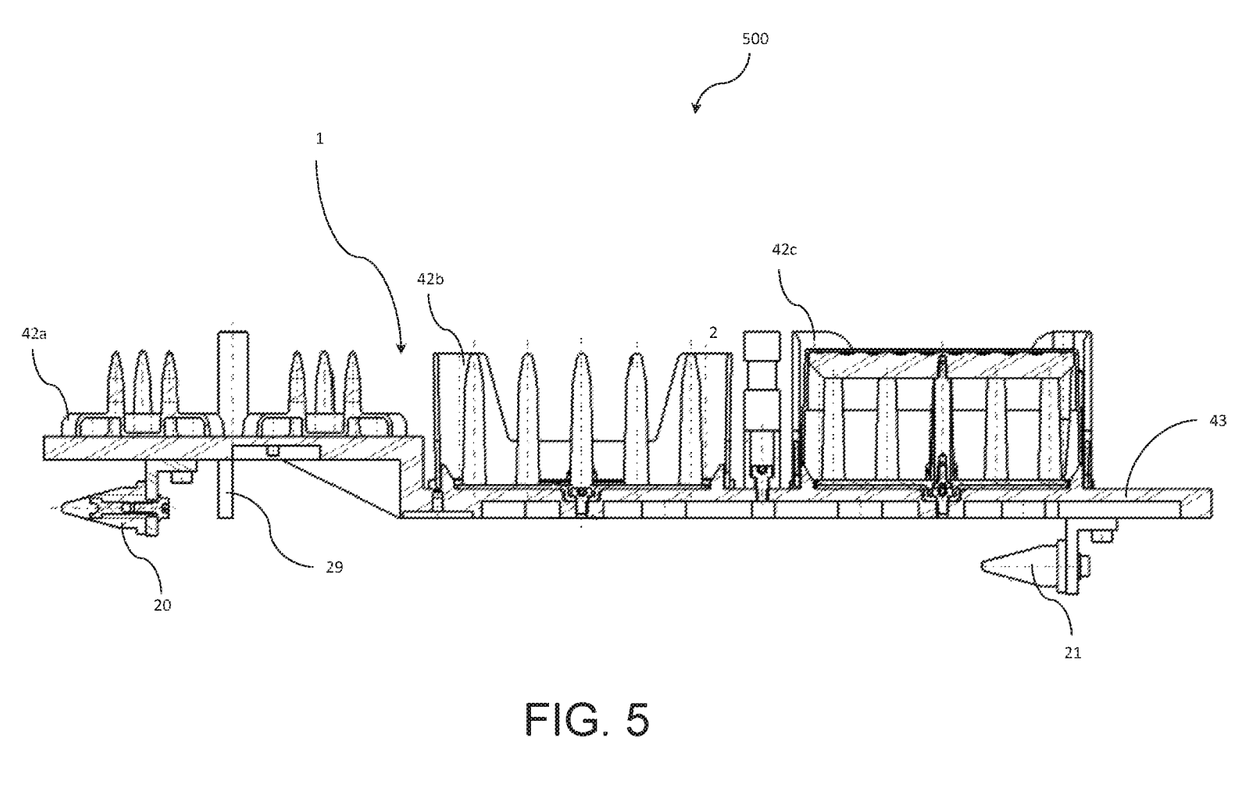
FIG. 5 illustrates a side view of the example holding structure of FIG. 4 according to an embodiment of the present disclosure.
Figure 6:
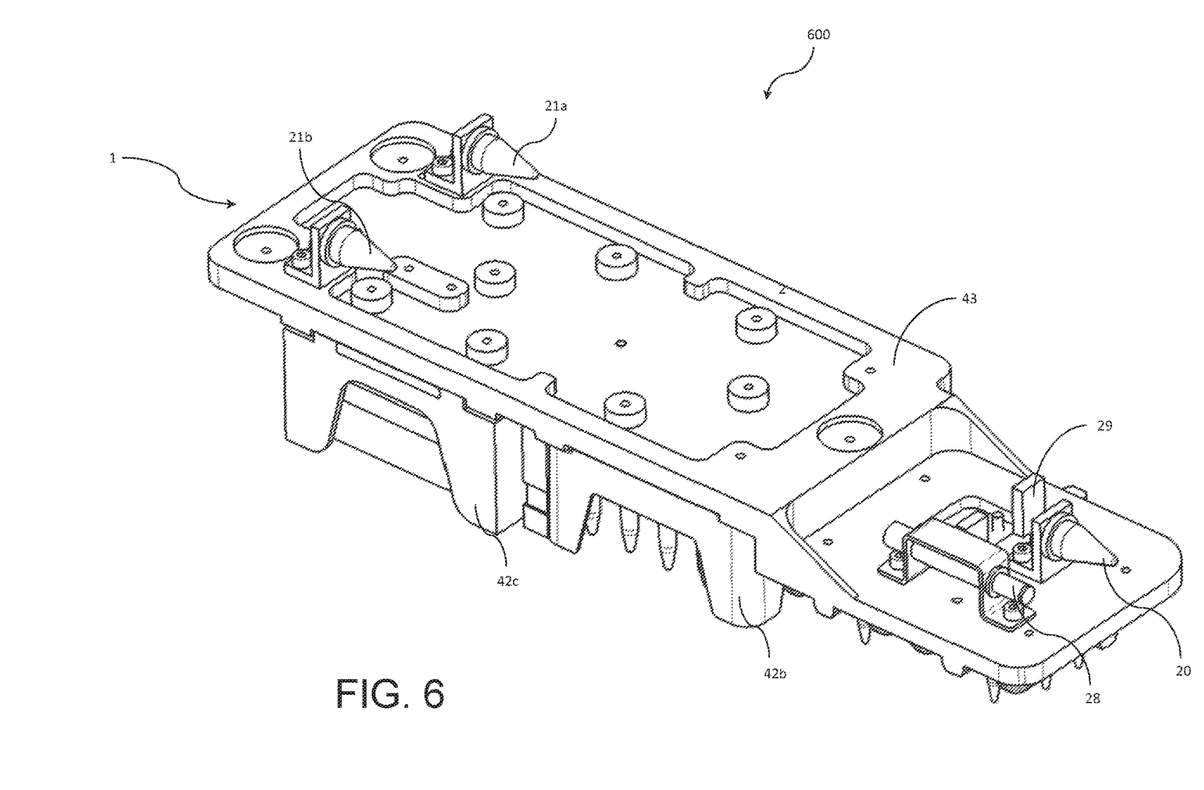
FIG. 6 illustrates a bottom view of the example holding structure of FIG. 4 according to an embodiment of the present disclosure.

FIGS. 4 to 6 depict different views of an example holding structure according to the present disclosure. As shown in FIG. 4, the holding structure can hold a plurality of receptacles 42c for material to be loaded into the device for loading an automated analysis system. As discussed above, in one example, an operator can store the material into the corresponding receptacles 42c when the drawer 2 is in a first position (e.g., an open position). Subsequently, the drawer 2 (or any alternative movable loading element) can move into the second position (e.g., a closed position). A manipulator (e.g., a robotic manipulator) can then manipulate the material.

The material to be loaded into automated analysis system can include consumables or disposables. For instance, the material to be loaded into automated analysis system can include one or more selected from the list comprising vessels, pipette tips and needles.

In some examples, as shown in FIG. 4, the receptacles 42c can have multiple parts. In FIG. 4 only one receptacle 42c is completely assembled to be filled with material (e.g., pipette tips). The other three receptacles 42a, 42b are depicted in a partially assembled state in FIG. 4 (whereas FIG. 2 depicts three receptacles 42a, 42b, 42c in a fully assembled state). As shown in FIG. 4, the receptacle can include a rack holder 53a, 53b, 54 fixedly attached to the holding structure. In the example of FIG. 4, the rack holder 53a, 53b, 54 can have pegs and corresponding recesses. These elements can allow for a precise relative placement of the respective rack holder 53a, 53b, 54. The rack holder 54 of the respective receptacle can hold a rack 55 in which material to be loaded into the automated analysis system can be stored.

The multipartite configuration of the receptacles shown in FIG. 4 can be varied in other examples. For instance, the receptacle can comprise a lower or larger number of parts. In one example, the receptacle can include a rack and a rack holding structure directly attached to the holding structure. In still other examples, a receptacle can be a single integral part.

The receptacles of the present disclosure can be configured to store any material required in an automated analysis system. For example, the receptacles can include one or more arrays of holders for pipette tips. In addition, the example holding structure 1 of FIG. 4 can include a rack for storing needles or other consumables. In other examples, the holder structure can be configured to hold a rack for storing vessels (e.g., test tubes) that can include material to be manipulated in the automated analysis system, or that can be filled with material in the automated analysis system. In still other examples, the material (e.g., the consumables) can be arranged in the receptacles in a different arrangement than in the two-dimensional arrays shown in FIGS. 2 and 4. For instance, the material can be stacked in other examples.

Further details of the receptacles 42a, 42b, 42c and their placement can be seen in FIG. 5. Even though the holding structure 1 of FIGS. 2 and 4 can hold four receptacles 42a, 42b, 42c a number, a shape and a type of the receptacles can be freely chosen depending on the particular application requirements.

In the example of FIG. 4, the receptacles 42a, 42b, 42c (e.g., including racks for pipette tips and vessels) can be releasably attached to the holding structure 1 by form-fitting the racks 55 to respective rack holders 54. In other examples, different fastening means can be used to fixedly attach the racks 55 to the corresponding rack holders 54 (e.g., screws, clips or magnets). In this manner, a predetermined holding structure 1 can be flexibly equipped with different types of receptacles depending on the particular application requirements. In addition, in the example of FIG. 4, each receptacle 42a, 42b, 42c can be equipped with an optional stabilizing structure 53a, 53b to stabilize a respective rack from below when a manipulator is lowered to manipulate material stored in the respective rack. In one example, the stabilizing structure 53a, 53b can include multiple pegs to stabilize the rack from below.

In other examples, the receptacles can be integrally formed with a part of the holding structure (e.g., a ground plate of the holding structure 1). Alternatively, the receptacles can be non-releasably attached to the holding structure 1. This can further improve the positioning precision of the material relative to the chassis. In still other examples, the receptacles can be attached to the holding structure 1 by placing them at a predetermined position.

Further aspects of the alignment elements attached to the holding structure 1 will be treated next in connection with FIGS. 5 and 6.

As already explained above, the example holding structure 1 of FIGS. 5 and 6, the alignment elements 20, 21a, 21b attached to the holding structure 1 can include conical pegs. Alignment of the holding structure 1 can be achieved by introducing the conical pegs 20, 21 into corresponding circular recesses (not shown in FIGS. 5 and 6) attached to the chassis. This can align the holding structure 1 relative to the chassis in all three spatial directions: On the one hand, the circular recesses can avoid movement in any direction perpendicular to the direction of movement of the drawer. In addition, a position in the direction of movement of the drawer can be specified by an inner circumference of the circular recess and an outer circumference of the conical pegs. The conical pegs can move through the circular recesses until they engage with an inner rim of the respective circular recess and further movement in the direction of travel of the drawer can be avoided. This can define the position in the direction of movement of the drawer (or alternative movable loading element).

The alignment elements of FIGS. 5 and 6 can facilitate alignment in all spatial directions. This can be required as the function of a manipulator of the automated analysis system can be compromised by deviations of the material's position from an expected position in all spatial directions. However, in other examples, it can suffice to align the chassis and the holding structure in in one or two spatial directions. For instance, it can be sufficient to align the holding structure and the chassis in the direction of travel of the drawer (or other movable loading element) and a second horizontal direction orthogonal to the direction of travel. In other examples, it can be sufficient to align the holding structure relative to the chassis in a vertical direction.

In these cases in which only alignment in a single or two directions can be required, the alignment elements can be adapted to allow for a larger play in the directions in which no particularly precise alignment is required. For instance, the alignment elements attached to the chassis can include an angled bracket with which a corresponding triangular alignment element of the holding structure can engage. This can align the holding structure and the chassis in two perpendicular directions. In another example, the alignment elements can include stops which only configured to align the holding structure in a single direction (e.g., a direction of travel of the movable loading element).

After having discussed variants of the functionality of the alignment elements, the shape and arrangement of the alignment elements will be discussed subsequently.

The figures of the present specification show alignment elements including conical pegs. As explained above, this configuration of the alignment elements can provide for a reliable alignment of the holding structure in all three spatial dimensions. However, the alignment elements used in the device for loading an automated analysis system according to the present disclosure can also have other shapes and configurations. In general, it can merely be required that the first alignment element and the second alignment element can engage and thereby align the holding structure relative to the chassis in the one or more (e.g., all three) spatial directions. For example, the first alignment element can include a first surface and the second alignment element can include a second, inverse surface. In other words, the first alignment element's surface can include a positive surface feature and the second alignment element can included a corresponding negative surface feature. The first and second alignment elements can be arranged so that the first and second surfaces of the first and second alignment elements can engage when the movable loading element has reached the second position.

For example, the first alignment element can have the form of a conus or a portion of a conus, a demi-sphere or a portion of a demi-sphere, a cylinder or a cuboid. The second alignment element can have a respective inverse shape. In one example, the second alignment element can include a circular recess, as shown in the figures of the present disclosure. In other examples, the second alignment element can include an annular element.

In some examples, the first alignment element can be a pin or peg and the second alignment element can be a recess. The recess formed by the second alignment element can have an inverse surface compared to the surface of the pin or peg. In other example, the recess can have a surface that corresponds to a portion of the outer surface of the pin or peg. For instance, the recess can have a circular surface. In another example, the first alignment element can include a hook configured to engage with a correspondingly formed second alignment element.

In the above examples, the first and second alignment elements can engage mechanically by moving into a predetermined position. However, in other examples according to the present disclosure, the alignment elements can engage by other forces. For instance, the first alignment element, the second alignment element, or both, can include a magnet arranged to engage with a magnetic element of a corresponding other alignment element to align the holding structure with the chassis.

In the following passages the arrangement of the first and second alignment elements will be discussed in more detail.

As can be seen in FIG. 6, the example holding structure can include three conical pegs 20, 21*a*, 21*b* as alignment elements. Two of these conical pegs 21*a*, 21*b* can be arranged at a rearward portion of the holding structure. The terms "rearward" and "forward" can be used in the present disclosure with respect to a direction of movement of the movable loading element (e.g., the drawer 2). The movable loading element can move in a "forward" direction when it is moved towards the second position (e.g., a closed position). Accordingly, a forward portion of an element or component can be the portion that is closest to the leading edge of the movable loading element when moving towards the second position (e.g., a closed position). Likewise, a rearward portion of an element or component can be the portion that is furthest away from the leading edge of the movable loading element when moving towards the second position (e.g., a closed position).

Moreover, the rearward conical pegs 21*a*, 21*b* can be arranged in positions near the sides of the holding structure 1 whereas the third conical peg 20 can be arranged in a more central position. In the example of FIG. 6, all alignment elements can be attached to the lower side of the groundplate 43 of the holding structures by a fastener (e.g., a screw).

By having three alignment elements distributed as discussed above, the holding structure of FIG. 6 can be aligned at three different points. This can further improve the alignment precision of the holding structure 1 relative to the chassis (not shown in FIG. 6). For instance, the holding structure 1 may deform or vibrate depending on, e.g., its geometry or load. As a result, certain portions of the holding structure 1 can move relative to the chassis even though one or more sets of alignment structures are engaged.

However, it may not be necessary to have three alignment elements (or any other particular number of alignment elements) attached to the holding structure. In some examples, the holding structure can be equipped with a single alignment element or two alignment elements. In other examples, the holding structure can be equipped with more than three alignment elements.

In addition or alternatively, the arrangement of the alignment elements can be freely chosen. In the example of FIG. 6, the alignment elements 20, 21*a*, 21*b* can be arranged in a triangular arrangement at the forward and rearward portions of the ground plate 43 of the holding structures. In other examples, the alignment structures can be arranged at one or both sides of the holding structure or at a top of the holding structure.

As can be seen in FIG. 5 and FIG. 6, the holding structure 1 can include a stop 29. The stop 29 can be arranged to provide a surface against which resilient element 23 (or any other retaining element coupled to the movable loading element) can be compressed. The resilient element 23 (or any other retaining element) can then exert a force on the stop 29. This force can keep the first alignment elements 5, 6 in engagement with second alignment elements 20, 21 when the movable loading element is in the second position. Optional aspects of the coupling between the resilient element 23 and the stop 29 are discussed below in connection with FIG. 7.

In some examples, the lower side of the ground plate of the holding structure can also include an optional additional damper 28 configured to dampen an impact when the alignment elements of the holding structure a device for loading an automated analysis system and the chassis move into engagement. This can be advantageous to avoid damage (e.g., to the movable loading element, the holding structure or material carried by the movable loading element) that might occur if the movable loading element is closed overly forcefully.

After having explained different aspects of the holding structure 1 in connection with FIGS. 4 to 6, further features of the drawer 2 (and movable loading element according to the present disclosure in general) will subsequently be detailed in connection with FIG. 7.

As already discussed, the movable loading element depicted in the figures of the present disclosure can be a drawer 2. Other configurations of movable loading element can also be used in combination with the floatingly coupled holding structure and the alignment elements of the present disclosure. For instance, the movable loading element can pivot or swivel between the first and second positions. In other examples, the movable loading element can also move linearly, but in a vertical direction (instead of the horizontal direction in which the drawer 2 moves).

The drawer 2 of FIG. 7 can include a handle 7 for actuating the drawer 2 manually. In addition, the drawer 2 can include a U-shaped main body 52 onto which the holding structure 1 (not shown in FIG. 7) can be floatingly mounted. The drawer 2 can have sliding elements arranged at each side of the U-shaped main body 52 (not shown in FIG. 7). These sliding elements can slide on corresponding rails attached to the chassis 3 of the device for loading an automated analysis system.

However, in other examples the drawer can be configured in a different manner than shown in FIG. 7. For example, the main body of the drawer can be substantially box-shaped, plate-shaped or have the form of an open frame.

In the example of FIG. 7, the body 52 of the drawer 2 can have multiple openings 61 through which the alignment elements of the holding structure can extend and by which the holding structure 1 can floatingly couple to the drawer 2.

Additionally or alternatively, as discussed above, the holding structure can be floatingly coupled to the drawer 2 in many different ways.

In the example of FIG. 7, a retaining element 23 can be attached to the drawer 2. As discussed above, the retaining element 23 can be configured to push the first and second alignment elements 5, 6, 20, 21 (not shown in FIG. 7) into engagement. The retaining element 23 of FIG. 7 can be configured to engage with a corresponding element attached to the holding structure. As can be seen in FIG. 7, the retaining element 23 can have an engagement element 59 which can be configured to engage with the corresponding stop 29 of the holding structure (e.g., a disc-shaped element having a groove to engage with a corresponding recess of the element attached to the holding structure). After the retaining element has been brought into engagement, further movement of the drawer 2 can result in a compression of the resilient element (e.g., a spring) included in the retaining element 23. The compressed resilient element can induce a force into the holding structure 1 which can contribute to bring the alignment elements into engagement.

In other examples, the retaining element can be configured to induce a pulling force instead of a pushing force into the holding structure. For instance, the retaining element can include a resilient element (e.g., a spring) which can be configured to expand after having engaged with a corresponding element of the holding structure. Then, the expanded resilient element can induce a pulling force into the holding structure which can pull the alignment elements into engagement.

In the above examples, retaining elements including a resilient element have been discussed. In other examples, the retaining elements can have other elements to keep the alignment elements in engagement. For instance, one or more magnets can be used as retaining elements. In addition or alternatively, an actively actuated retaining element (e.g., actuated by an electric actuator) may keep the alignment elements in engagement (e.g., similar to the locking device 24 discussed in connection with FIG. 1 above).

In still other examples, the drawer can be equipped with multiple retaining elements. In addition or alternatively, the arrangement of the retaining element and the corresponding element of the holding structure can be reversed. Additionally or alternatively, the retaining elements can be an integral part of the alignment elements (e.g., a retaining element can be a magnet integrated into an alignment element).

Furthermore, in some examples, the device for loading an automated analysis system can have no dedicated retaining element. For example, the alignment elements might generate enough holding force to keep themselves in engagement. In one example, the alignment elements can generate sufficient stiction to avoid that the movable loading element moves when the material in in the receptacles is manipulated (i.e., the stiction is sufficiently high such that it cannot be overcome by forces induced when the material is manipulated by an automated analysis system the movable loading element is attached to). For example, the alignment elements can have one or more elements on the surface of the alignment elements being made from a different material than the remainder of the surface of the respective alignment element.

Figure 8:
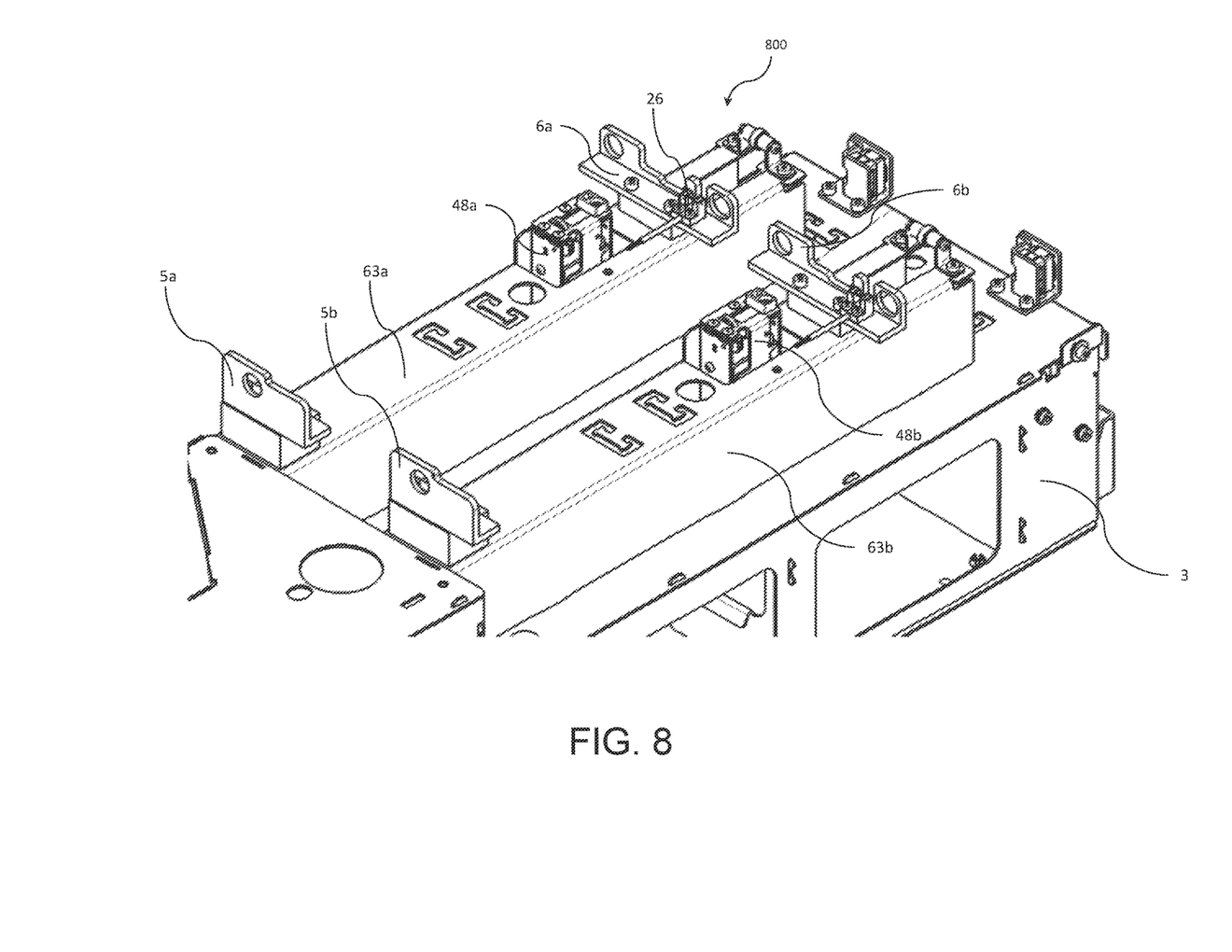
FIG. 8 illustrates an example chassis of a device for loading an automated analysis system according to an embodiment of the present disclosure.

FIG. 8 depicts an example chassis 3 of a device for loading an automated analysis system according to the present disclosure. The chassis 3 of FIG. 8 can include two guide structures 63a, 63b. On each guide structure 63a, 63b a drawer 2 can be movably mounted. Furthermore, as already explained, the chassis 3 can be equipped with multiple alignment elements 5a, 5b, 6a, 6b. In general, the device for loading an automated analysis system according to the present disclosure can include two or more movable loading elements having respective alignment elements. In addition, the chassis 3 can include locking devices 24a, 24b for locking the drawer 2 (not shown in FIG. 8) relative to the chassis 3. These components will be discussed in more detail subsequently.

The alignment elements 5a, 5b, 6a, 6b can include circular recesses for engaging with the conical pegs discussed above. The alignment elements 5a, 5b, 6a, 6b of FIG. 8 can include brackets which can be secured to the respective guide structure 63a, 63b at one side and can include the respective circular recess at a second side. As can be seen in FIG. 8, two alignment elements 6a, 6b can be arranged to engage with respective alignment element attached to a rearward portion of the drawer 2 can be formed as a single element.

However, the arrangement and configuration of the alignment elements 5a, 5b, 6a, 6b of the chassis 3 can be different in other examples. For example, the alignment elements themselves can have any of the forms discussed above in connection with alignment elements attached to the movable loading element (e.g., the drawer). In addition or alternatively, the alignment elements 5a, 5b, 6a, 6b of the chassis 3 can be attached to different parts of the chassis 3 (which might itself have a different configuration than the configuration of FIG. 8). For example, the alignment elements 5a, 5b, 6a, 6b of the chassis 3 can be arranged at a side of a guide structure 63a, 63b to guide a loading element. In other examples, the alignment elements 5a, 5b, 6a, 6b of the chassis 3 can subtend over a guide structure 63a, 63b to guide a loading element. In addition or alternatively, the alignment elements 5a, 5b, 6a, 6b can be arranged at different positions at the guide structure 63a, 63b. For examples, the alignment elements 5a, 5b, 6a, 6b can be arranged only at a central portion of the guide structure 63a, 63b. The number of the alignment elements 5a, 5b, 6a, 6b can also be different than the number of alignment elements 5a, 5b, 6a, 6b shown in FIG. 8 (e.g., there can be one, two or more than three alignment elements).

The chassis of FIG. 8 can host two movable loading elements (e.g., drawers). In other examples, the chassis 3 can host only one movable loading element or more than two movable loading elements. In addition or alternatively, the movable loading elements and thus the respective elements of the chassis 3 can be of different size, of different configuration, or both. In one example, a first drawer can be larger than a second drawer movably coupled to the chassis.

The device for loading of the present disclosure can include a sensor element 26 for detecting a position of the movable loading element (e.g., a drawer) relative to the chassis 3. For example, the sensor element can include an optoelectronic sensor. In FIG. 8, a sensor 26 can be attached to each of the rearward alignment elements 6a, 6b. The sensor 26 can be configured to sense when a tab (or another element attached to the drawer) attached to the drawer 2 moves in a predetermined position. For instance, the sensor 26 can be configured to sense changing optical properties when the tab (or the other element) attached to the drawer 2 moves in a predetermined position.

As a response to the sensor 26 signaling that the drawer 2 has reached the predetermined position, the device for loading material of the present disclosure can engage the respective locking element 24a, 24b to lock the respective drawer 2 relative to the chassis 3.

Reference throughout the preceding specification to "one embodiment", "an embodiment", "one example" or "an example", "one aspect" or "an aspect" can mean that a particular feature, structure or characteristic described in connection with the embodiment or example can be included in at least one embodiment of the present invention. Thus, appearances of the phrases "in one embodiment", "in an embodiment", "one example" or "an example", "one aspect" or "an aspect" in various places throughout this specification are not necessarily all referring to the same embodiment or example.

Furthermore, the particular features, structures, or characteristics may be combined in any suitable combinations and/or sub-combinations in one or more embodiments or examples.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for loading an automated analysis system, the device comprising:
    a chassis;
    a movable loading element movably coupled to the chassis and configured to move along a longitudinal axis between a first and a second position;
    a holding structure, the holding structure being floatingly coupled to the movable loading element so that the holding structure can move in one or more orthogonal directions relative to the longitudinal axis when the movable loading element is in the first position, wherein the holding structure is configured to hold a receptacle for material to be loaded into the automated analysis system;
    two or more first alignment elements attached to the chassis arranged at different locations of the chassis; and
    two or more second alignment elements attached to the holding structure, the first and second alignment elements being arranged at different locations of the chassis and the holding structure, respectively, wherein at least one of the second alignment elements is arranged at a forward portion of the holding structure and at least a second one of the second alignment elements is arranged at a rearward portion of the holding structure in the longitudinal direction of movement of the movable loading element,
    wherein each of the first alignment elements is configured to engage with a respective one of the second alignment element to align the holding structure in a predetermined position relative to the chassis when the movable loading element is in the second position.

2. The device for loading an automated analysis system according to claim 1, wherein the movable loading element is a drawer.

3. The device for loading an automated analysis system according to claim 1, wherein the second position of the movable loading element occurs when the movable loading element decouples from the holding structure and is in a closed position of the movable loading element.

4. The device for loading an automated analysis system of claim according to claim 1, wherein each of the second alignment elements includes a peg.

5. The device for loading an automated analysis system according to claim 4, wherein the peg is a conical peg.

6. The device for loading an automated analysis system according to claim 1, wherein each of the first alignment elements includes a recess configured to receive the second alignment element.

7. The device for loading an automated analysis system according to claim 6, wherein the recess is a hole configured to receive a corresponding member of the second alignment element.

8. The device for loading an automated analysis system according to claim 1, wherein the holding structure is aligned in all three spatial directions by a peg when the movable loading element is in the second position.

9. The device for loading an automated analysis system according to claim 1, further comprising, a retaining element configured to keep the first alignment elements in engagement with second alignment elements when the holding structure is in the predetermined position.

10. The device for loading an automated analysis system according to claim 1, further comprising a locking device for locking the movable loading element to the chassis when the movable loading element is in the second position.

11. The device for loading an automated analysis system according to claim 1, further comprising a self-closing mechanism for moving the movable loading element over at last part of its travelling path into the second position comprising a first element attached to the chassis and a second element attached to the movable loading element, wherein the first element and the second element contact and engage each other as the movable loading element approaches the second position.

12. The device for loading an automated analysis system according to claim 11, wherein the self-closing mechanism is a mechanical self-closing mechanism.

* * * * *